United States Patent
Takei et al.

(10) Patent No.: US 10,010,382 B2
(45) Date of Patent: Jul. 3, 2018

(54) PISTON EASILY MOUNTABLE TO CARTRIDGE AND METHOD OF INSERTING THE PISTON

(71) Applicant: SHOFU INC., Kyoto-shi, Kyoto (JP)

(72) Inventors: Ryouji Takei, Soka (JP); Akira Yoneda, Soka (JP); Shuji Sakamoto, Kyoto (JP); Yusei Kadobayashi, Kyoto (JP)

(73) Assignee: SHOFU INC., Kyoto-Shi (JP)

( * ) Notice: Subject to any disclaimer, the term of this patent is extended or adjusted under 35 U.S.C. 154(b) by 0 days.

(21) Appl. No.: 15/206,447

(22) Filed: Jul. 11, 2016

(65) Prior Publication Data

US 2017/0014205 A1    Jan. 19, 2017

(30) Foreign Application Priority Data

Jul. 14, 2015 (JP) .................................. 2015-140835

(51) Int. Cl.
| | |
|---|---|
| *A61C 5/06* | (2006.01) |
| *B65B 3/00* | (2006.01) |
| *B65B 3/12* | (2006.01) |
| *A61C 5/62* | (2017.01) |

(52) U.S. Cl.
CPC ................ *A61C 5/062* (2013.01); *A61C 5/62* (2017.02); *B65B 3/003* (2013.01); *B65B 3/12* (2013.01)

(58) Field of Classification Search
CPC B65B 3/003; B65B 3/12; A61C 5/062; A61C 5/62; A61C 5/64; A61C 5/66; A61C 5/68
See application file for complete search history.

(56) References Cited

U.S. PATENT DOCUMENTS 3,346,147 A * 10/1967 Higgins ............ B05C 17/00593
    222/326
4,492,576 A *  1/1985 Dragan ................ A61C 9/0026
    433/90

(Continued)

FOREIGN PATENT DOCUMENTS

| EP | 2 578 181 A1 | 4/2013 |
|---|---|---|
| EP | 2 853 225 A1 | 4/2015 |
| JP | 10-179608 | 7/1998 |

OTHER PUBLICATIONS

European Search Report dated Mar. 1, 2017.

*Primary Examiner* — Timothy L Maust
*Assistant Examiner* — Andrew StClair
(74) *Attorney, Agent, or Firm* — Rankin, Hill & Clark LLP (57) ABSTRACT

A paste-type dental material is filled from an opening portion of a cartridge into a cylindrical portion by moving the opening portion of the cylindrical portion of the cartridge along a kneading surface, on which the paste-type dental material is kneaded, with the opening portion being inclined. The piston is placed on the kneading surface with a circular end surface of the piston contacting the kneading surface. The piston is inserted into the cylindrical portion by moving the opening portion of the cylindrical portion of the cartridge closer to the piston located on the kneading surface such that a piston-side tapered surface or the piston-side curved surface of the piston is fitted into the opening portion, and thereafter moving the one of the two ends of the cylindrical portion toward the kneading surface.

1 Claim, 11 Drawing Sheets

(56) References Cited

U.S. PATENT DOCUMENTS

| | | | |
|---|---|---|---|
| 5,324,273 A * | 6/1994 | Discko, Jr. | B05C 17/00593 433/90 |
| 5,893,714 A * | 4/1999 | Arnold | A61C 5/62 433/90 |
| 6,379,152 B1 * | 4/2002 | Dragan | A61C 5/66 433/90 |
| 8,556,870 B2 * | 10/2013 | Fundingsland | A61C 5/62 433/90 |
| 2002/0076671 A1 | 6/2002 | Evers et al. | |
| 2003/0100866 A1 * | 5/2003 | Reynolds | A61J 1/062 604/187 |

* cited by examiner

| EX. | A | B | C | A/B | A/C | EXTRUDABILITY | LIQUID LEAKAGE | EASE OF PISTON INSERTION |
|---|---|---|---|---|---|---|---|---|
| 1 | 3.65 | 1.47 | 3.50 | 2.48 | 1.04 | OK | OK | ○ |
| 2 | 3.65 | 4.50 | 3.50 | 0.81 | 1.04 | OK | OK | ○ |
| 3 | 3.60 | 1.47 | 3.50 | 2.45 | 1.03 | OK | OK | ○ |
| 4 | 3.60 | 4.50 | 3.50 | 0.80 | 1.03 | OK | OK | ○ |
| 5 | 4.10 | 5.00 | 4.00 | 0.82 | 1.03 | OK | OK | ○ |
| 6 | 4.10 | 4.00 | 4.00 | 1.03 | 1.03 | OK | OK | ○ |
| 7 | 4.05 | 3.00 | 4.00 | 1.35 | 1.01 | OK | OK | ○ |
| 8 | 4.05 | 1.80 | 4.00 | 2.25 | 1.01 | OK | OK | ○ |
| 9 | 7.35 | 2.94 | 7.00 | 2.50 | 1.05 | OK | OK | ○ |
| 10 | 7.35 | 8.88 | 7.00 | 0.83 | 1.05 | OK | OK | ○ |
| 11 | 7.10 | 2.94 | 7.00 | 2.41 | 1.01 | OK | OK | ○ |
| 12 | 7.10 | 8.88 | 7.00 | 0.80 | 1.01 | OK | OK | ○ |
| COM. EX.1 | 4.00 | 2.00 | 3.50 | 2.00 | 1.14 | NG | OK | ○ |
| 2 | 3.30 | 2.00 | 3.50 | 1.65 | 0.94 | OK | NG | × |
| 3 | 4.10 | 6.00 | 4.00 | 0.68 | 1.03 | OK | OK | ○ |
| 4 | 4.10 | 1.00 | 4.00 | 4.10 | 1.03 | OK | NG | ○ |
| 5 | 4.00 | 6.00 | 4.00 | 0.67 | 1.00 | OK | NG | × |

PISTON EASILY MOUNTABLE TO CARTRIDGE AND METHOD OF INSERTING THE PISTON

TECHNICAL FIELD

The present invention relates to a method of filling a paste-type dental material into a cartridge which includes a cartridge body including a cylindrical portion having an opening portion to which a piston is mounted after the paste-type dental material is filled into the cartridge through the opening portion, and to a cartridge suitable to implement the method.

BACKGROUND ART

JP 10-179608 A describes in FIGS. 1A-1F an example cartridge according to the related art. The cartridge includes: a cartridge body made of a resin and including a cylindrical portion 1 having two ends and an opening portion at one of the two ends and a nozzle body portion 2 disposed at the other of the two ends of the cylindrical portion 1 and provided with a nozzle; and a piston 13 made of a resin and disposed inside the cylindrical portion 1 of the cartridge body to push out a content contained in the cylindrical portion 1 through the nozzle. The thickness of the piston 13 is larger than the radial dimension of the cartridge. In the disclosed cartridge, a pair of piston-side tapered surfaces 15 are formed between an annular peripheral wall surface of the piston and a pair of circular end surfaces of the piston located on both sides in the thickness direction of the piston, and the pair of piston-side tapered surfaces 15 become smaller in radial dimension from the annular peripheral wall surface toward the pair of circular end surfaces.

SUMMARY OF INVENTION

Technical Problem

To insert the piston after filling a paste-type dental material into the cylindrical portion of the conventional cartridge described in JP 10-179608 A, an operator picks up the piston with his/her fingers to insert the piston into the cylindrical portion through the opening portion of the cylindrical portion. With this method, however, inserting the piston becomes more difficult as the piston is smaller.

An object of the present invention is to provide a method of filling a paste-type dental material into a cartridge which facilitates inserting a piston after a paste-type dental material is filled into the cartridge, and a cartridge suitable to implement the method.

Solution to Problem

The present invention provides a method of filling a paste-type dental material into a cartridge which includes a cartridge body made of a resin and including a cylindrical portion having two ends and an opening portion at one of the two ends and a nozzle portion provided at the other of the two ends of the cylindrical portion, and a piston made of a resin and disposed inside the cylindrical portion to push out a content contained in the cylindrical portion of the cartridge body through the nozzle portion. A pair of piston-side tapered surfaces or piston-side curved surfaces are formed between an annular peripheral wall surface of the piston and a pair of circular end surfaces of the piston located on both sides in a thickness direction of the piston. The pair of piston-side tapered surfaces or piston-side curved surfaces become smaller in radial dimension from the annular peripheral wall surface toward the pair of circular end surfaces.

The method according to the present invention includes: filling the paste-type dental material from the opening portion of the cartridge into the cylindrical portion by moving the opening portion of the cylindrical portion of the cartridge along a kneading surface such as a kneading board, on which the paste-type dental material is kneaded, with the opening portion being inclined; placing the piston on the kneading surface with the circular end surface of the piston contacting the kneading surface; and inserting the piston into the cylindrical portion by moving the opening portion of the cylindrical portion of the cartridge close to the piston located on the kneading surface such that the piston-side tapered surface or the piston-side curved surface of the piston is fitted into the opening portion, and thereafter moving the one end of the cylindrical portion toward the kneading surface. According to the present invention, the piston is inserted into the opening portion of the cartridge without the operator picking up the piston with his/her fingers, and thus inserting the piston can be easily performed even if the piston is small in size.

In a cartridge for use in the method of filling a paste-type dental material according to the present invention, preferably, a body-side tapered surface or a body-side curved surface is formed at the opening portion at the one end of the cylindrical portion of the cartridge body, and the body-side tapered surface or the body-side curved surface becomes smaller in radial dimension toward the other end of the cylindrical portion. Preferably, an inner angle of the body-side tapered surface or a radius of curvature of the body-side curved surface is larger than the inner angle of the pair of piston-side tapered surfaces or the radius of curvature of the pair of piston-side curved surfaces formed on the piston. If a ratio A/B between a radial dimension A of the piston and a thickness B of the piston is $2.5 \geq A/B > 0.8$ and, in particular, a ratio A/C between the radial dimension A of the piston and the inside diameter C of the cylindrical portion is $1.05 \geq A/C > 1.0$, the piston placed on the kneading surface does not easily fall over, which stabilizes the workability of inserting the piston.

BRIEF DESCRIPTION OF DRAWINGS

FIG. 4B is a vertical sectional view illustrating the applicator mounted with the cartridge when the plunger is pushed in.

FIG. 6 is an enlarged vertical sectional view illustrating a main portion of the applicator mounted with the cartridge when the plunger is pushed in.

DESCRIPTION OF EMBODIMENTS

Now, an embodiment of the present invention will be described in detail below with reference to the accompanying drawings. In the following description, an exemplary embodiment of the present invention will be described in detail while describing a dental applicator for use to discharge a paste-type dental material from a cartridge into which the paste-type dental material has been filled according to the present invention. FIGS. 1A to 1F are a front view, a bottom view, a plan view, a left side view, a right side view, and a perspective view, respectively, illustrating that a cartridge 3 is mounted to an applicator 1. The applicator 1 is constituted from a cylindrical syringe 5 and a plunger 7. In FIG. 1, the plunger 7 is located at a stand-by position as discussed later.

<Cartridge>

Figure 7A:
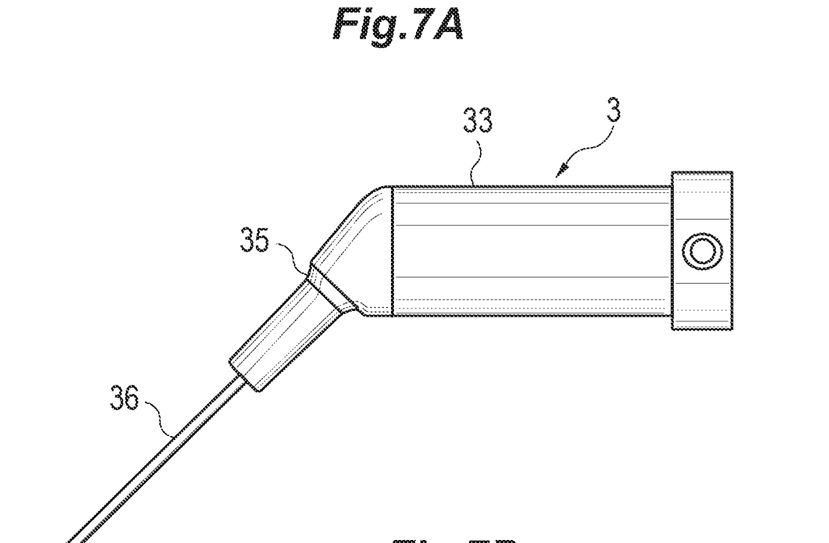
FIG. 7A is a front view of the cartridge.
Figure 7B:
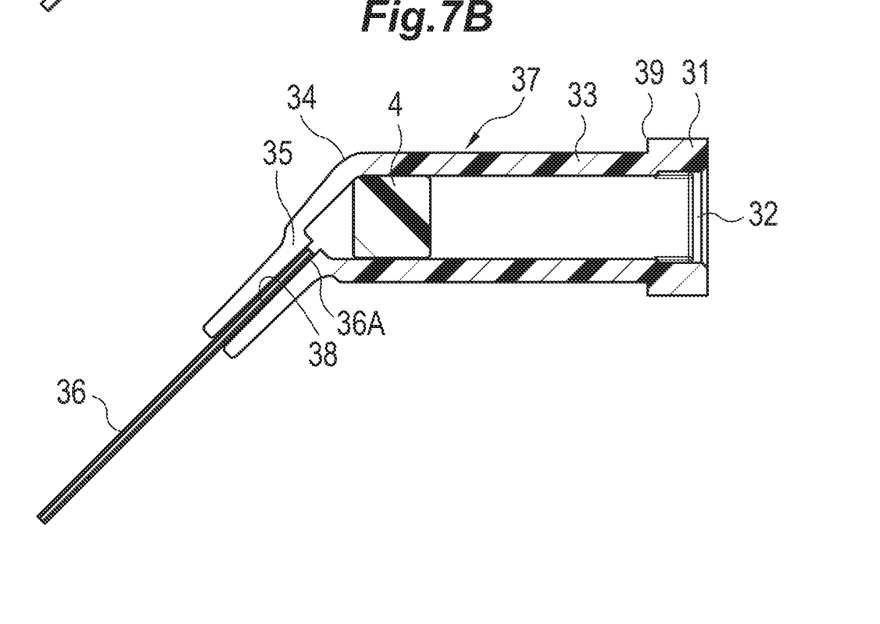
FIG. 7B is a vertical sectional view of the cartridge.
Figure 8:
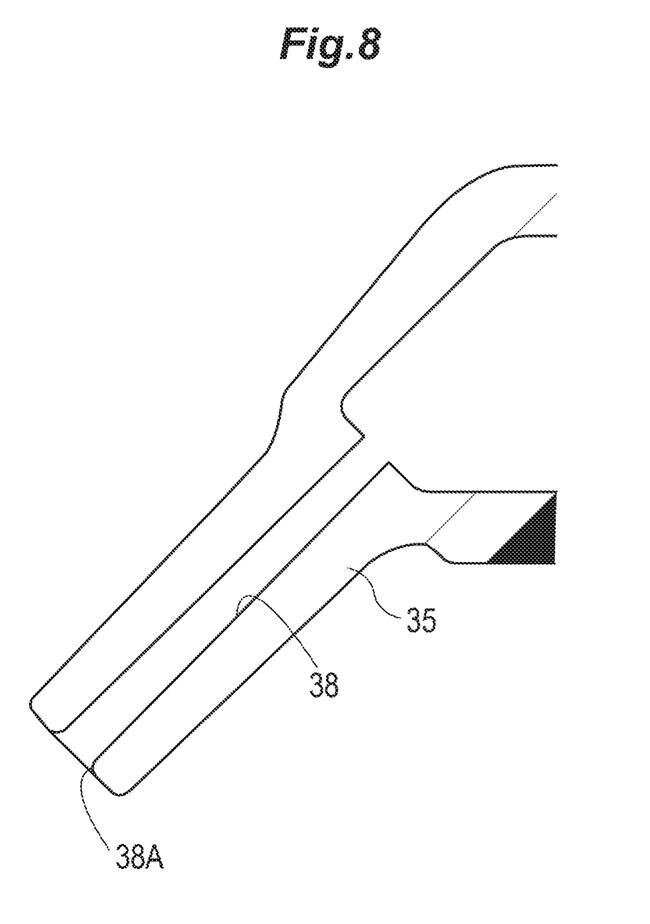
FIG. 8 is an enlarged vertical sectional view of a nozzle portion of the cartridge.

As illustrated in FIGS. 7A and 7B, the cartridge 3 includes a cylindrical portion 33 having two ends and an opening portion 32 and a flange portion 39 formed at one 31 of the two ends of the cylindrical portion 33, a nozzle portion 35 provided at the other 34 of the two ends of the cylindrical portion 33, and the piston 4 disposed inside the cylindrical portion 33 to push out a content contained in the cylindrical portion 33 from the nozzle portion 35. The nozzle portion 35 includes, as a nozzle, a pipe 36 made of metal and provided at the other end 34 of the cylindrical portion 33. The cylindrical portion 33 and the nozzle portion 35 are integrally molded from a resin material such as polypropylene. Preferably, an entire surface of the end portion 36A of the pipe 36 is curved such that no angled portion is present. With this configuration, it is possible to prevent the inner wall of a through hole 38 from being shaved by the pipe 36 when inserting the pipe 36 into the through hole 38, thereby furthermore preventing the swarf from being produced and pushed out as mixed in the content. As illustrated in FIG. 8, an annular tapered surface 38A is formed at an entrance portion of the through hole 38, and the tapered surface 38A becomes larger in radial dimension toward an opening end surface of the entrance portion. The tapered surface 38A is formed not to contact the outer peripheral surface of the pipe 36 when the pipe 36 is press-fitted into the through hole 38. Such a tapered surface 38A facilitates insertion of the pipe 36 into the through hole 38.

The through hole 38 is shaped such that the radial dimension of the through hole 38, which extends in the longitudinal direction of the nozzle portion 35 continuously with the tapered surface 38A, becomes gradually smaller and thereafter constant. With this configuration, the pipe 36 can be easily inserted to the middle of the through hole 38, after which the pipe 36 is press-fitted, thereby alleviating the workload of press-fitting.

Figure 9A:
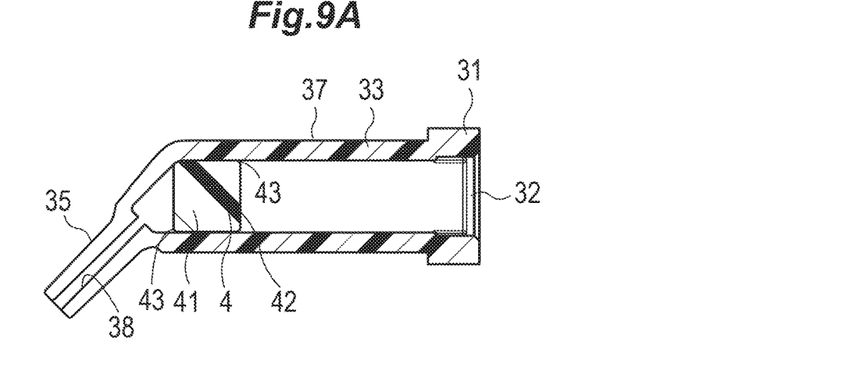
FIGS. 9A and 9B are a vertical sectional view and a horizontal sectional view, respectively of the cartridge.
Figure 9B:
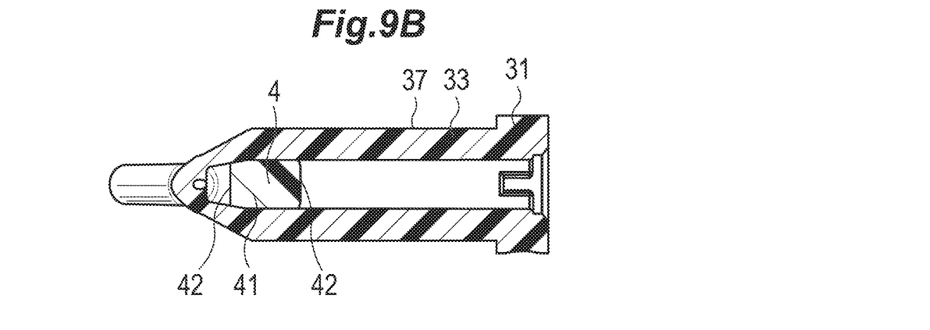
Figure 9C:
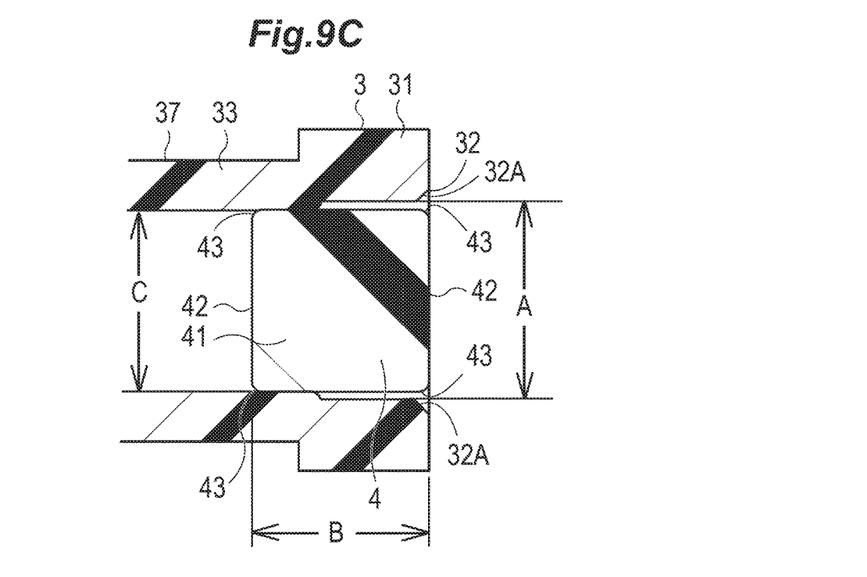
FIG. 9C is a sectional view illustrating a main portion of the applicator including a piston.

The piston 4 is integrally molded from a resin material such as polypropylene. As illustrated in FIGS. 9A to 9C, a pair of piston-side tapered surfaces 43 or piston-side curved surfaces 43 are formed between an annular peripheral wall surface 41 of the piston 4 and a pair of circular end surfaces 42, 42 of the piston 4 located on both sides in the thickness direction of the piston 4. The pair of piston-side tapered surfaces 43 or piston-side curved surfaces 43 become smaller in radial dimension from the annular peripheral wall surface 41 toward the pair of circular end surfaces 42, 42. In FIGS. 9A and 9B, one of the end portions of the piston 4 has been deformed to conform to the shape of the inner wall surface of the cylindrical portion 33 of a cartridge body 37.

As illustrated in FIG. 9C, a body-side tapered surface 32A or a body-side curved surface 32A is formed at the opening portion 32 at the one end of the cylindrical portion 33 of the cartridge body 37, and the body-side tapered surface 32A or the body-side curved surface 32A becomes smaller in radial dimension toward the other end of the cylindrical portion 33. The inner angle of the body-side tapered surface 32A or the radius of curvature of the body-side curved surface 32A is larger than the inner angle of the pair of piston-side tapered surfaces 43 or the radius of curvature of the pair of piston-side curved surfaces 43 formed on the piston 4. This configuration further facilitates insertion of the piston 4 from the opening portion 32 of the cylindrical portion 33.

It has been verified through a test that, if a ratio A/B between a radial dimension A of the piston 4 and a thickness B of the piston 4 is 2.5≥A/B>0.8 and, in particular, a ratio A/C between the radial dimension A of the piston 4 and the inside diameter C of the cylindrical portion 33 is 1.05≥A/C>1.0, the piston 4 placed on the kneading surface does not easily fall over, which stabilizes the workability of inserting the piston.

<Method of Inserting Piston>

Figure 10A:
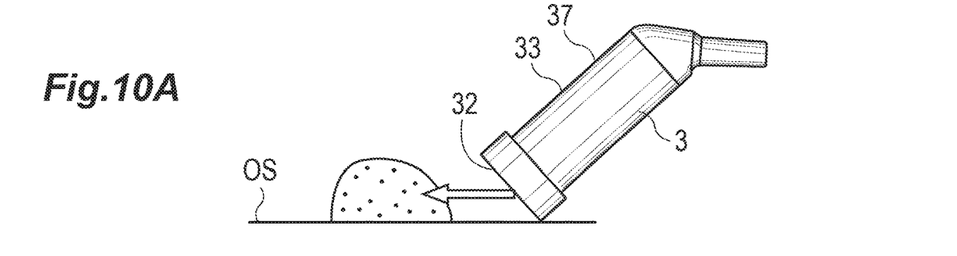
FIGS. 10A to 10D illustrate operation that occurs when a content is filled into the cartridge.
Figure 10B:
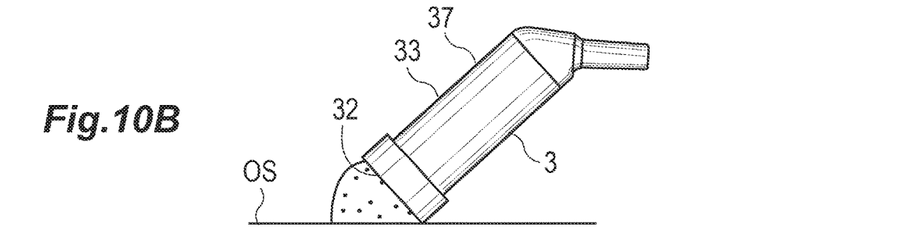
Figure 10C:
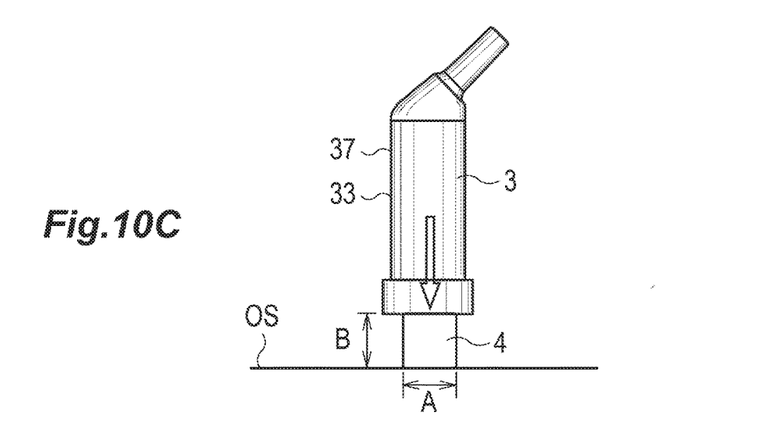
Figure 10D:
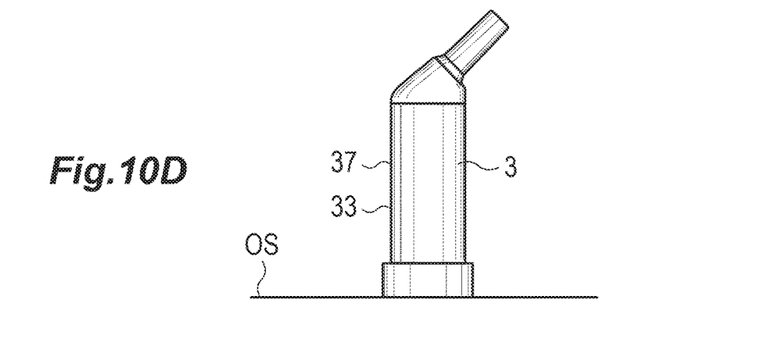

A content is filled into the cartridge body 37 as follows. First, as illustrated in FIGS. 10A and 10B, the paste-type dental material is filled from the opening portion 32 of the cartridge body 37 into the cylindrical portion 33 by moving the opening portion 32 along a kneading surface OS, on which the paste-type dental material is kneaded, with the opening portion 32 being inclined. This filling operation is performed at least once, usually a plurality of times. The opening portion 32 may be pressed against the kneading surface OS in the filling operation. Next, as illustrated in FIG. 10C, the piston 4 is placed on the kneading surface OS with the circular end surface 42 (see FIGS. 5A and 9C) of the piston 4 contacting the kneading surface OS. Then, as illustrated in FIG. 10D, the piston 4 is inserted into the cylindrical portion 33 by moving the opening portion 32 of the cartridge 3 close to the piston 4 located on the kneading surface OS such that the piston-side tapered surface 43 (see FIGS. 5A and 9C) or the piston-side curved surface 43 (see FIGS. 5A and 9C) of the piston 4 is fitted into the opening portion 32, and thereafter moving the one end of the cylindrical portion 33 toward the kneading surface OS. With this configuration, the piston 4 is inserted into the opening portion 32 of the cartridge 3 without the operator touching the piston 4 with his/her fingers, and thus inserting the piston 4 can be easily performed even if the piston 4 is small in size.

<Verification Test>

Figure 11:
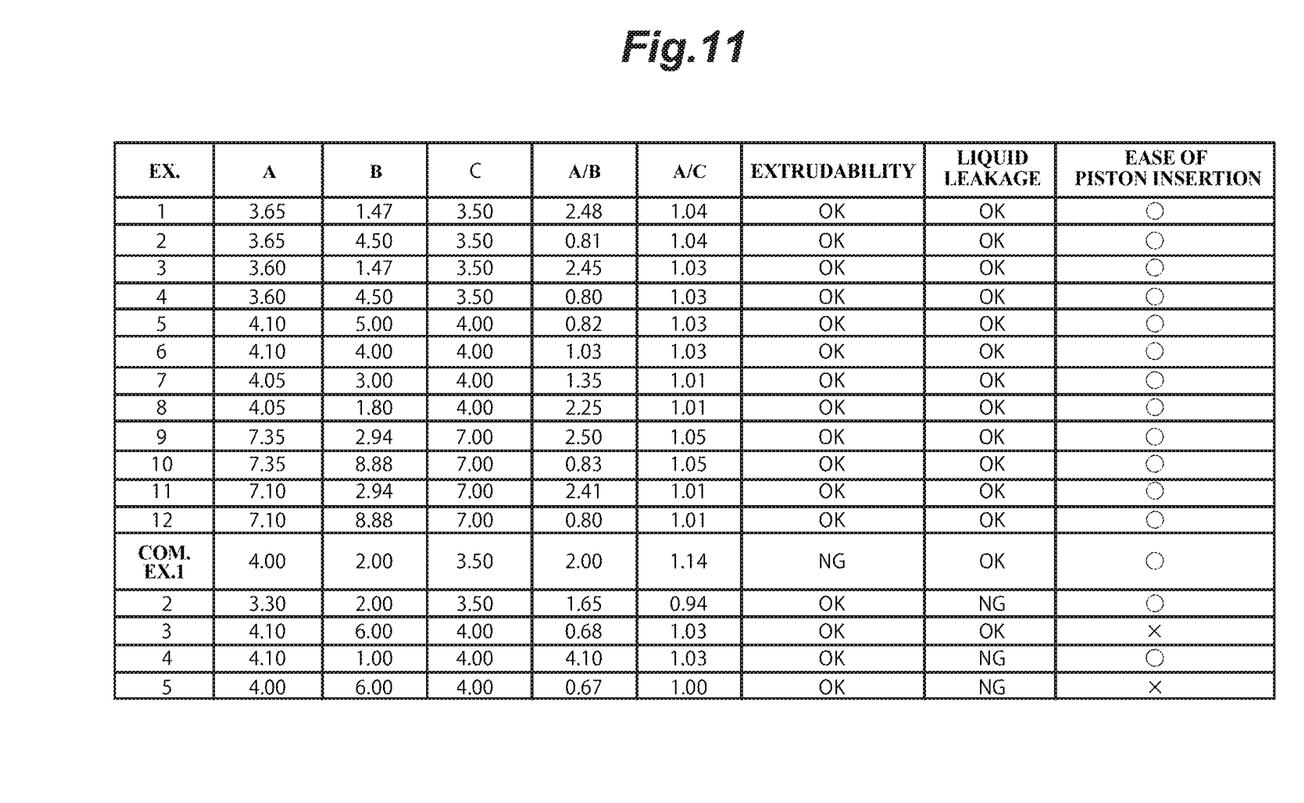
FIG. 11 illustrates the results of experiments.

The test results for examples and comparative examples of the cartridge according to the present invention will be specifically described below. The present invention is not limited to such examples. The performance of the cartridge 3 and the piston 4 according to the examples was evaluated by the following test method. The test results are illustrated in FIG. 11.

[Extrudability]

Purpose: to evaluate the ease of pushing out the content using the cartridge 3 and the piston 4.

Method: Hy-Bond Glasionomer CX was prepared with the compounding ratio of powder material:liquid material=2.0:1.0 (0.20 g:0.10 g) on a kneading board, and was kneaded for 40 seconds using a plastic spatula. The kneaded object was filled from the opening portion of the cylindrical portion 33 of the cartridge into the cartridge by moving the opening portion along the kneading surface OS of the kneading board with the opening portion being inclined and partly contacting the kneading board. After that, the piston 4 was inserted into the cartridge 3 by pressing the opening portion 32 of the cartridge 3, into which the kneaded object had been filled, against the piston 4 which was stationary on the kneading surface OS. Further, the cartridge into which the piston had been inserted was mounted to the applicator 1. The ease of pushing out the kneaded object using the plunger 7 was verified. The extrudability was evaluated in the following two levels.

OK: the kneaded object was easily pushed out.

NG: it was hard or impossible to push out the kneaded object.

[Leakage of Kneaded Object]

Purpose: to evaluate the leakage of the kneaded object from the periphery of the piston that occurs when the content is extruded using the cartridge 3 and the piston 4.

Method: Hy-Bond Glasionomer CX was prepared with the compounding ratio of powder material:liquid material=2.0:1.0 (0.20 g:0.10 g) on a kneading board, and was kneaded for 40 seconds using a plastic spatula. The kneaded object was filled from the opening portion of the cartridge into the cartridge by moving the opening portion along the kneading surface of the kneading board with the opening portion being inclined and partly contacting the kneading board. After that, the piston 4 was inserted into the cartridge 3 by pressing the opening portion of the cartridge 3, into which the kneaded object had been filled, against the piston 4 which was stationary on the kneading surface. Further, the cartridge 3 into which the piston had been inserted was mounted to the applicator 1. It was verified to see if the kneaded object leaked from the periphery of the piston when the kneaded object was pushed out using the plunger 7. The leakage of the kneaded object was evaluated in the following two levels.

OK: no leakage of the kneaded object was found.

NG: the kneaded object leaked from the periphery of the piston.

[Ease of Piston Insertion]

Purpose: to evaluate the ease of inserting the piston with the kneaded object filled in the cartridge 3.

Method: Hy-Bond Glasionomer CX was prepared with the compounding ratio of powder material:liquid material=2.0:1.0 (0.20 g:0.10 g) on a kneading surface of a kneading board, and was kneaded for 40 seconds using a plastic spatula. The kneaded object was filled from the opening portion of the cartridge 3 into the cartridge 3 by moving the opening portion along the kneading board with the opening portion being inclined and partly contacting the kneading board. After that, the piston 4 was inserted into the cartridge 3 by pressing the opening portion of the cartridge 3, into which the kneaded object had been filled, against the piston 4 which was stationary on the kneading board. The ease of inserting the piston 4 was verified. The ease of inserting the piston 4 was evaluated in the following three levels.

Criterion for Evaluation: the number of times that the piston fell over and was not insertable.

○: none

Δ: once to three times

×: four times or more

It has been verified from the test results in FIG. 11 that, if a ratio A/B between a radial dimension A of the piston 4 and a thickness B of the piston 4 is $2.5 \geq A/B > 0.8$ and, in particular, a ratio A/C between the radial dimension A of the piston 4 and the inside diameter C of the cylindrical portion 33 is $1.05 \geq A/C > 1.0$, the piston 4 placed on the kneading surface OS does not easily fall over, which stabilizes the workability of inserting the piston 4.

<Applicator>

Now, an applicator 1 for use in the experiments will be described below. The applicator 1 includes the cylindrical syringe 5 and the plunger 7. As illustrated in FIGS. 1A-1F and 2A-2D, the cylindrical syringe 5 is integrally molded from a resin material such as polypropylene or polyethylene, and has two ends. The cylindrical syringe 5 includes a cartridge fitting portion 52 provided at one 50 of the two ends of the cylindrical syringe 5 and configured to be fitted with the cartridge 3. As illustrated in FIGS. 1A-1F and 3A-3D, the plunger 7 is integrally molded from a resin material such as polypropylene or polyethylene, and has two ends. The plunger 7 includes a pressing portion 72 provided at one 71 of the two ends of the plunger 7 and configured to be inserted into the cylindrical syringe 5 from the other 53 of the two ends of the cylindrical syringe 5 and to press a piston 4 inside the cartridge 3 fitted with the cartridge fitting portion 52, and an operated portion 74 provided at the other 73 of the two ends of the plunger 7, extending through the other end 53 of the cylindrical syringe 5, and configured to be pressed by a finger of an operator. The cylindrical syringe 5 and the plunger 7 are each molded integrally from a resin material, which makes it possible to significantly reduce the price of the applicator 1 compared to the conventional ones.

In the present embodiment, a stopper portion 76 that abuts on the other end 53 of the cylindrical syringe 5 is provided in the vicinity of the operated portion 74 of the plunger 7. Providing such stopper portion 76 in this way prevents the operator from pushing the plunger 7 too far into the cylindrical syringe 5 to break the plunger 7 or the cylindrical syringe 5 which is made of a resin material. The plunger 7 is shaped such that the outer peripheral surface of a portion 77 that is adjacent to the stopper portion 76 is proximate to the inner peripheral surface of the cylindrical syringe 5. With adoption of such structure, the plunger 7 can be stably moved along the cylindrical syringe 5 when the plunger 7 is pushed in. As a result, the plunger 7 is not swung when the plunger 7 is pushed in, thereby improving the operability of the applicator 1. In addition, the plunger 7 advantageously does not easily slip out of the cylindrical syringe 5.

<Resistance Structure>

In the present embodiment, as illustrated in FIGS. 4A-4B, 5A-5B, and 6, a resistance structure (54, 75) is provided between the inner peripheral surface of the cylindrical syringe 5 and the outer peripheral surface of the pressing portion 72 of the plunger 7. The resistance structure (54, 75) acts as resistance to movement of the pressing portion 72 when the pressing portion 72 is moved toward the cartridge fitting portion 52 beyond a predetermined position P shown in FIG. 5A and to movement of the pressing portion 72 when the pressing portion 72 is moved from the side of the cartridge fitting portion 52 toward the other end 53 of the cylindrical syringe 5 beyond the predetermined position P. The resistance structure (54, 75) is configured to allow the pressing portion 72 to be moved beyond the predetermined position P against the resistance when a force equal to or greater than a predetermined force is applied to the plunger 7 in the longitudinal direction of the plunger 7.

Figure 5A:
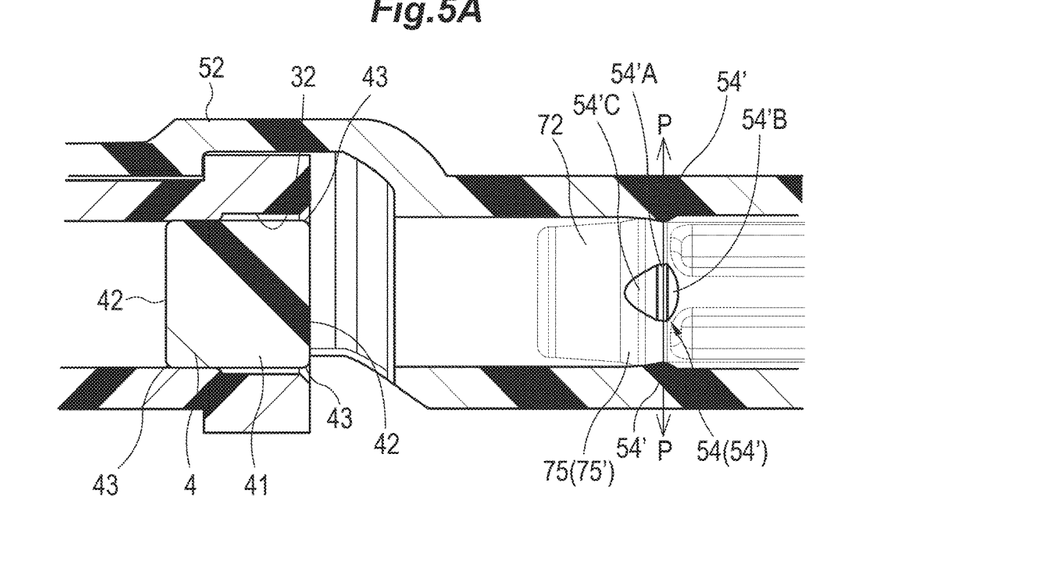
FIG. 5A is an enlarged sectional view illustrating a main portion of the applicator mounted with the cartridge when the plunger is withdrawn; an upper part of FIG. 5B is an enlarged view illustrating the shape of a distributed projecting portion; and a lower part of FIG. 5B is a sectional view as taken along line C-C of the upper part of FIG. 5B.
Figure 6:
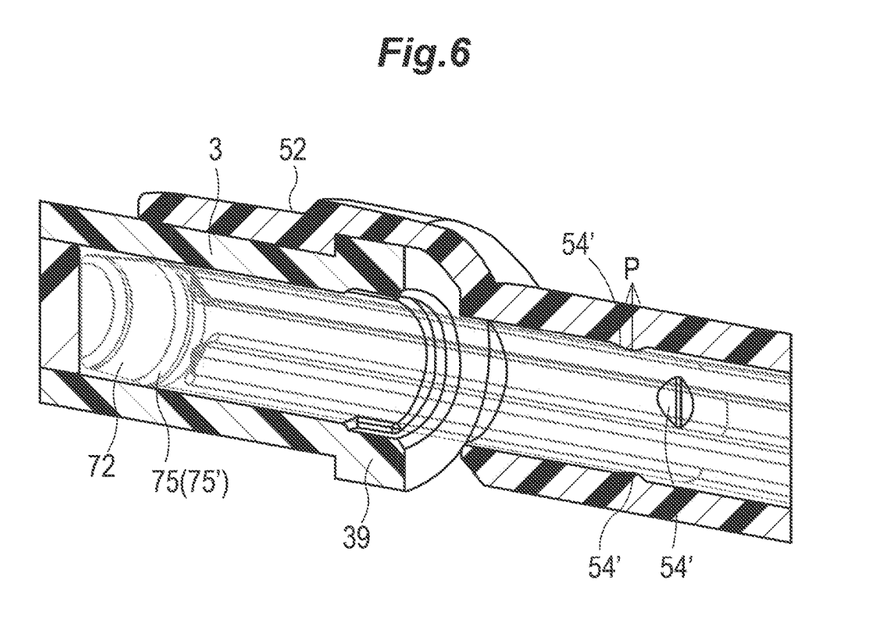

In the embodiment, as illustrated enlargedly in FIGS. 5A and 6, the resistance structure (54, 75) includes at least one outer projecting portion 54 integrally formed with the inner peripheral surface of the cylindrical syringe 5 to project radially inward, and at least one inner projecting portion 75 integrally formed with the outer peripheral surface of the pressing portion 72 of the plunger 7 to project radially outward. The resin material for forming the cylindrical syringe 5 and the shape of the at least one outer projecting portion 54 and the resin material for forming the plunger 7 and the shape of the at least one inner projecting portion 75 are determined such that the at least one inner projecting portion 75 and the at least one outer projecting portion 54 are deformed to allow the at least one inner projecting portion 75 to pass over the at least one outer projecting portion 54 when a force equal to or greater than the predetermined force is applied to the plunger 7. The resin materials are preferably polypropylene. With this configuration, the inner projecting portion 75 and the outer projecting portion 54, which are constituents required for the resistance structure (54, 75), can be integrally formed with the cylindrical syringe 5 and the plunger 7, respectively, when the cylindrical syringe 5 and the plunger 7 are molded.

As illustrated in FIGS. 3A-3D, 5A, and 6, the at least one inner projecting portion 75 provided on the plunger 7 is constituted from one annular projecting portion 75' that continuously annularly extends on the outer peripheral surface of the pressing portion 72 of the plunger 7, and the cross-sectional shape of the annular projecting portion 75' has a mountain-like profile of which the height gradually increases continuously toward the apex of the profile, as the annular projecting portion 75' is cut in a direction orthogonal to the circumferential direction of the plunger 7. The at least one outer projecting portion 54 is constituted from four distributed projecting portions 54' provided at predetermined angular intervals in the circumferential direction. The cross-sectional shape of each distributed projecting portion 54' has a profile of which the height gradually increases continuously toward the apex of the profile, as the distributed projecting portions 54' are cut in a direction orthogonal to the circumferential direction of the cylindrical syringe 5. The cross-sectional shape of each distributed projecting portion 54' has a profile of which the height gradually increases continuously toward the apex of the profile, as the distributed projecting portions 54' are cut in the circumferential direction of the cylindrical syringe 5. The predetermined angular intervals between the plurality of distributed projecting portions 54' may be determined as desired, but are preferably 60°, 90°, or 120°. With these angles, both high molding precision and high strength can be easily achieved even if the cylindrical syringe 5 and the plunger 7 are molded from a resin material.

Figure 1A:
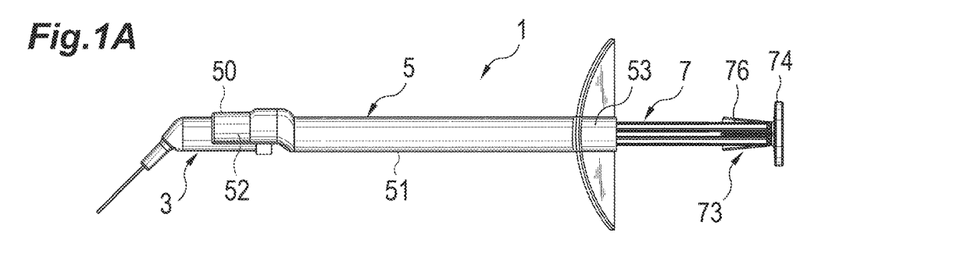
FIGS. 1A to 1F are a front view, a bottom view, a plan view, a left side view, a right side view, and a perspective view, respectively, illustrating that an applicator is mounted with a cartridge.
Figure 1B:
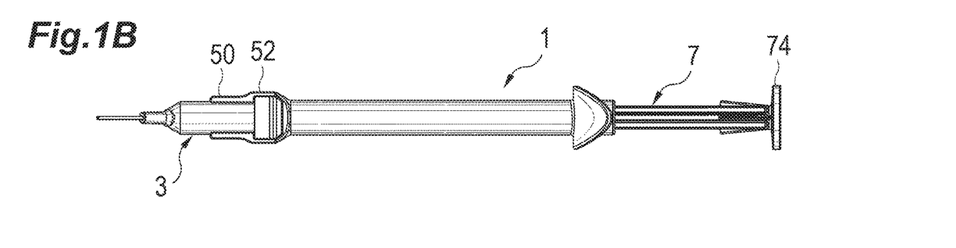
Figure 1C:
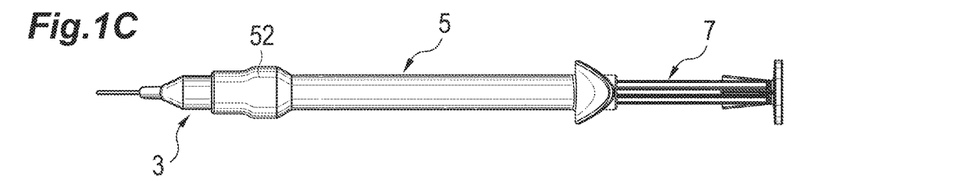
Figure 1D:
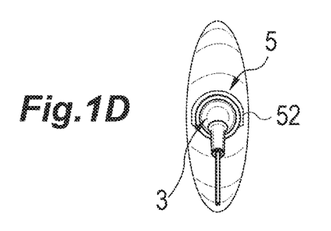
Figure 1E:
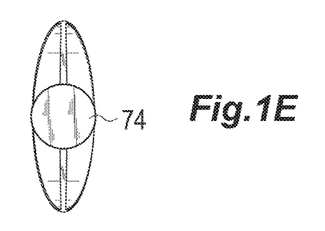
Figure 1F:
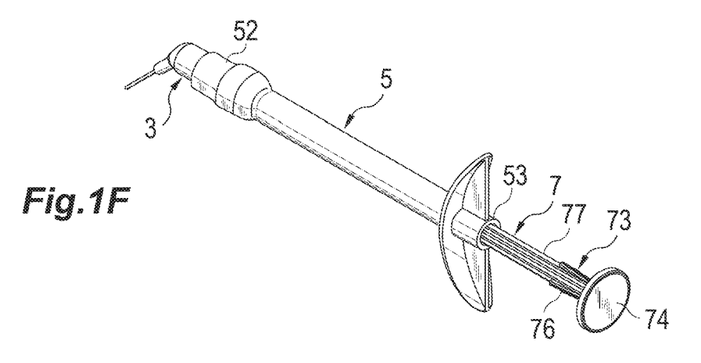
Figure 5B:
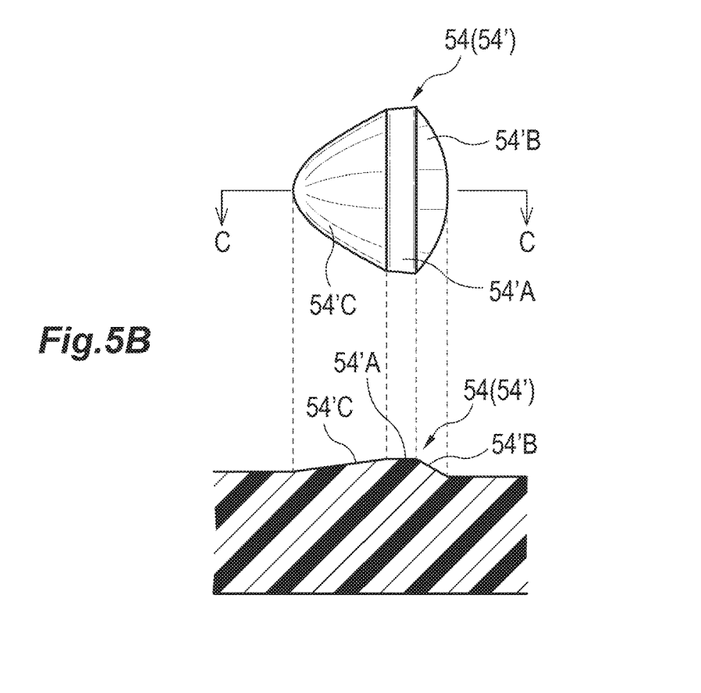

As illustrated enlargedly in FIG. 5B, the profile of each distributed projecting portion 54' has a flat portion 54'A provided at the apex of the profile, and a skirt 54'C formed on the side of the cartridge fitting portion 52 [see FIG. 1A] with respect to the flat portion 54'A is longer than a skirt 54'B formed on the side of the other end 53 [see FIG. 1A] of the cylindrical syringe 5 with respect to the flat portion 54'A. If the distributed projecting portions 54' include the flat portion 54'A, the apexes of the distributed projecting portions 54' are more uniformly worn when either one of the annular projecting portion 75' and the four distributed projecting portions 54' passes over the other. This prevents the apexes of the distributed projecting portions 54' from being worn out early even if an action of either one of the annular projecting portion and the plurality of distributed projecting portions passing over the other or a converse action is repeatedly performed a certain number of times. As a result, the applicator 1 can be used a plurality of times even if the cylindrical syringe 5 and the plunger 7 are molded from a resin material. Providing the flat portion 54'A on each distributed projecting portion 54' can increase the processing precision of the distributed projecting portion 54'.

In contrast, the resistance structure according to the embodiment described above, the at least one outer projecting portion 54 may be constituted from one annular projecting portion that continuously annularly extends on the inner peripheral surface of the cylindrical syringe 5, and the cross-sectional shape of the annular projecting portion may have a mountain-like profile of which the height gradually increases continuously toward the apex of the profile, as the annular projecting portion is cut in a direction orthogonal to the circumferential direction of the cylindrical syringe 5. In this configuration, the at least one inner projecting portion 75 may be constituted from a plurality of distributed projecting portions provided at predetermined angular intervals in the circumferential direction of the plunger 7, and the cross-sectional shape of each distributed projecting portion may have a profile of which the height gradually increases continuously toward the apex of the profile, as the distributed projecting portions are cut in the direction orthogonal to the circumferential direction of the plunger 7 and the cross-sectional shape of each distributed projecting portion may have a profile of which the height gradually increases continuously toward the apex of the profile, as the distributed projecting portions are cut in the circumferential direction of the plunger 7.

In a configuration as in the present embodiment, wherein the resistance structure (54, 75) is constituted from the one annular projecting portion 75' and the plurality of distributed projecting portions 54', the annular projecting portion 75' and the plurality of distributed projecting portions 54' can be easily deformed when a force equal to or greater than a predetermined force is applied to the plunger 7 in the longitudinal direction of the plunger 7 as either one of the annular projecting portion 75' and the plurality of distributed projecting portions 54' passes over the other. In contrast, after either one of the annular projecting portion 75' and the plurality of distributed projecting portions 54' has passed over the other, either one of the annular projecting portion 75' and the plurality of distributed projecting portions 54' does not pass over the other in the opposite direction, even if the plunger 7 is rotated in the cylindrical syringe 5, unless a predetermined force is applied to the plunger 7 in the longitudinal direction of the plunger 7. Thus, the plunger 7 can be prevented from slipping off with a simple structure.

The position P of the resistance structure (54, 75) may be determined as desired. Preferably however, the resistance structure is provided adjacent to the cartridge fitting portion 52 of the cylindrical syringe 5 as in the present embodiment. If the resistance structure is located at the position P, it is possible to reduce the distance by which the plunger 7 is moved downward from the cylindrical syringe 5 when the operator holds the applicator 1 with the plunger 7 being directed downward, thereby improving the operability of the applicator 1. In practice, the resistance structure (54, 75) is preferably positioned such that the cartridge 3 can be fitted with the cartridge fitting portion 52 and the cartridge 3 can be removed from the cartridge fitting portion 52 when the at least one inner projecting portion 75 of the plunger 7 is in contact with the at least one outer projecting portion 54. With this configuration, the cartridge 3 can be mounted and removed without removing the plunger 7.

<Structure of Cartridge Fitting Portion>

Figure 2A:
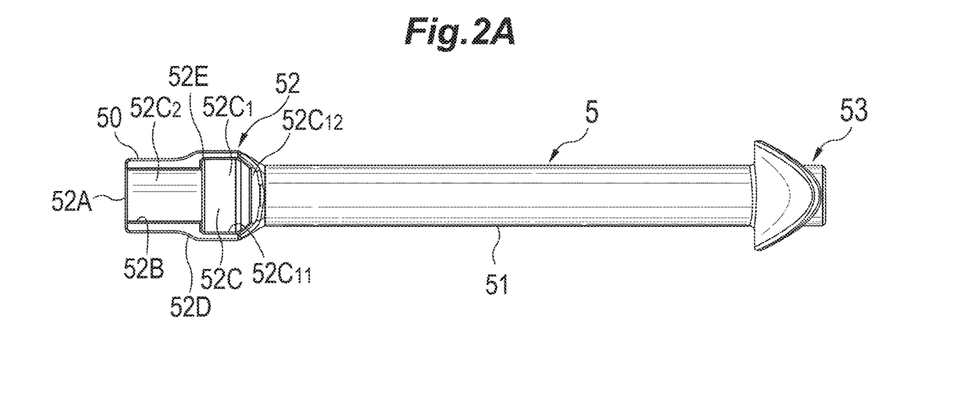
FIGS. 2A to 2D are a bottom view, a right side view, a left side view, and a perspective view, respectively, of a cylindrical syringe.
Figure 2B:
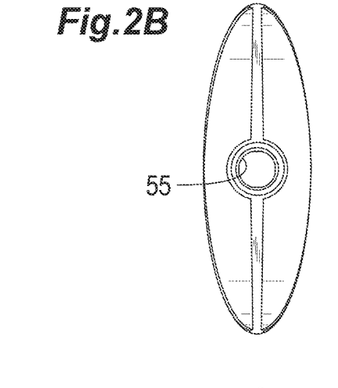
Figure 2C:
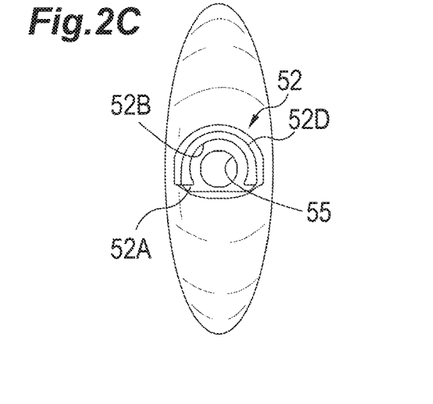
Figure 2D:
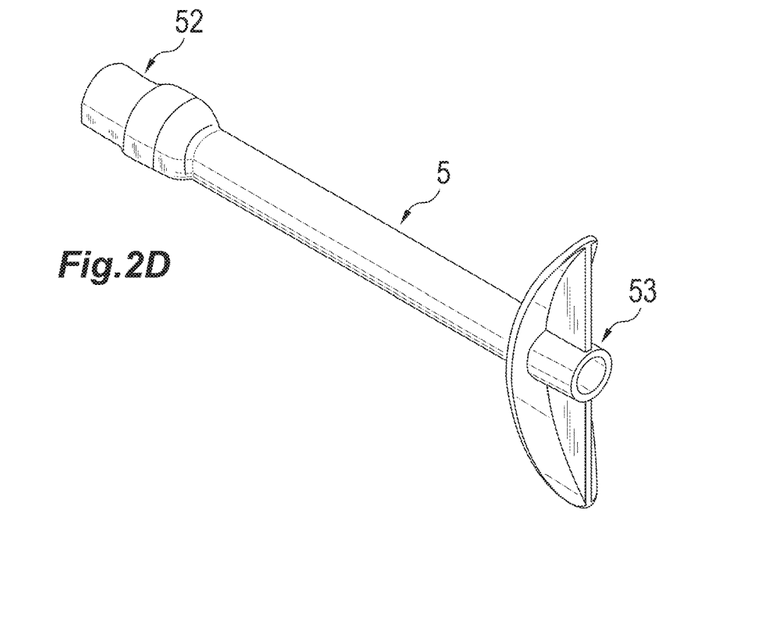
Figure 3A:
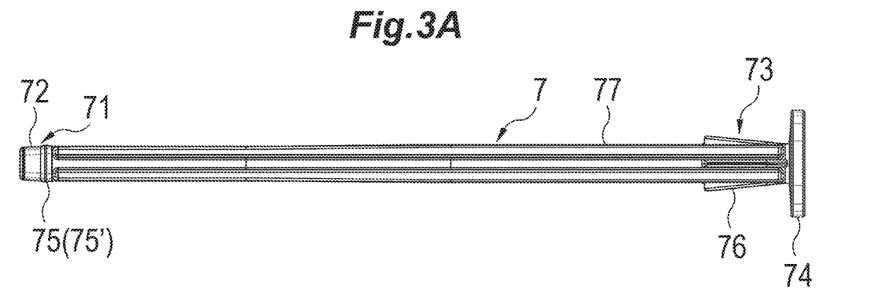
FIGS. 3A to 3D are a front view, a left side view, a right side view, and a perspective view, respectively, of a plunger.
Figure 3B:
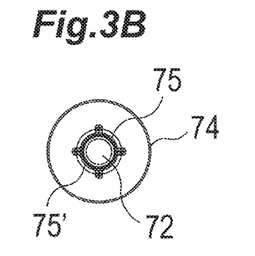
Figure 3C:
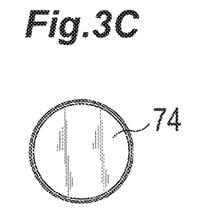
Figure 3D:
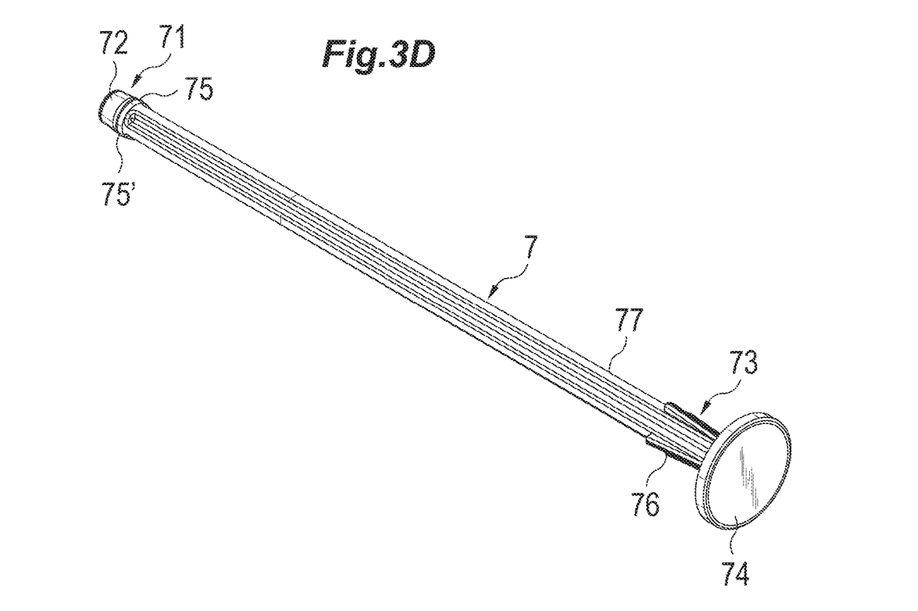
Figure 4A:
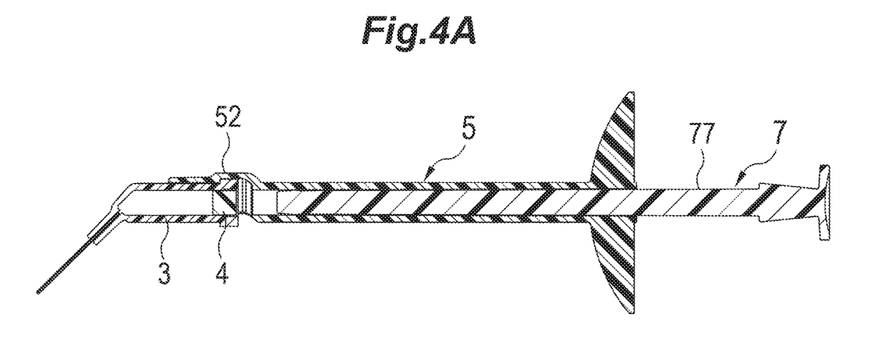
FIG. 4A is a vertical sectional view illustrating the applicator mounted with the cartridge when the plunger is withdrawn.
Figure 4B:
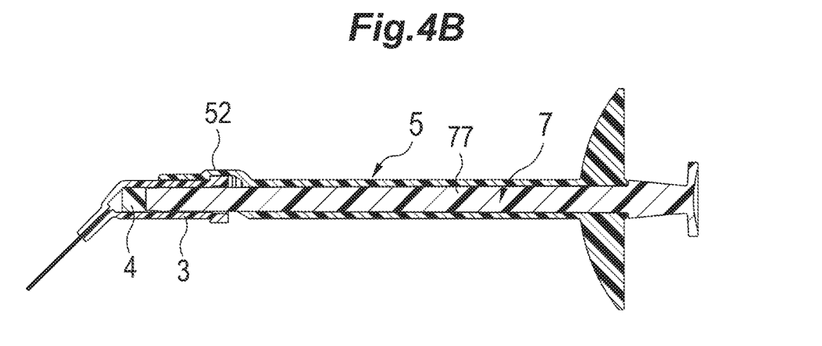

As illustrated in FIGS. 2A and 2B, the cartridge fitting portion 52 configured to be fitted with the cartridge 3 includes an end surface opening portion 52A opened in an extending direction in which a cylindrical body 51 of the cylindrical syringe 5 extends, a continuous opening portion 52B continuous with the end surface opening portion 52A, opened in a radial direction, and extending in the extending direction, and a recess portion 52C configured to communicate with the continuous opening portion 52B and an internal passage 55 in the cylindrical body 51. The recess portion 52C includes a flange fitting recess 52C1 to be fitted with the flange portion 39 of the cartridge 3, and a cylindrical portion fitting recess 52C2 configured to communicate with the flange fitting recess 52C1 and to be fitted with a part of the cylindrical portion 33. A wall portion 52D surrounding the cylindrical portion fitting recess 52C2 of the cartridge fitting portion 52 is configured to warp into snap engagement with the part of the cylindrical portion 33 when the part of the cylindrical portion 33 is inserted from the continuous opening portion 52B. Specifically, a sectional shape of an inner wall surface of the wall portion 52D surrounding the cylindrical portion fitting recess 52C2 has an arcuate profile that is continuous with the continuous opening portion 52B, as the wall portion 52D is cut in a direction orthogonal to a longitudinal direction of the cylindrical syringe 5, and the arcuate profile has an arcuate angle larger than 180 degrees. With such a structure, a sufficient force for holding the cylindrical portion 33, which is required for snap engagement, can be secured. The term "snap engagement" refers to engagement obtained when the wall portion 52D surrounding the cylindrical portion fitting recess 52C2 holds the cylindrical portion 33 utilizing a force generated in the wall portion 52D which has been deformed to be opened and then is going to return to its original state. The flange fitting recess 52C1 includes a first portion 52C11 to be fitted with the flange portion 39, and a second portion 52C12 located between the flange portion 39 and the cylindrical body 51 when the first portion 52C11 is fitted with the flange portion 39. In the present embodiment, the second portion 52C12 is shaped to become gradually smaller in radial dimension as the second portion 52C12 extends toward the cylindrical body 51. The wording "(to be) shaped to become gradually smaller in radial dimension" may mean in other words that the inner wall surface of a wall portion surrounding the second portion 52C12 of the flange fitting recess 52C1 constitutes a part of a conical surface having its apex located on the side of the cylindrical body 51.

A stepped portion 52E to be engaged with the flange portion 39 is formed between the flange fitting recess 52C1 and the cylindrical portion fitting recess 52C2. The stepped portion 52E is configured to entirely contact the end surface of the flange portion 39 located on the side of the cylindrical portion 33. With adoption of this structure, the flange portion 39 is pressed against the stepped portion 52E when the piston 4 is pushed by the plunger 7, thereby preventing the cartridge 3 from popping out of the cartridge fitting portion 52.

While the preferred embodiments of the present invention have been described and shown herein, the present invention should not be construed in a limiting sense. It should be understood that various modifications, rearrangements, and substitutions may be made without departing from the scope of the present invention.

INDUSTRIAL APPLICABILITY

According to the present invention, it is possible to provide a method of filling a paste-type dental material into a cartridge, which facilitates inserting a piston into the cartridge after the paste-type dental material has been filled into the cartridge, and a cartridge suitable for use with the method.

What is claimed is:

1. A method of filling a paste dental material into a cartridge, the method comprising:
    providing a cartridge and a piston, said cartridge including a cartridge body made of a resin and including a cylindrical portion having two ends and an opening portion at one of the two ends, and a nozzle portion provided at the other of the two ends of the cylindrical portion, said cartridge having a body-side tapered surface or a body-side curved surface formed at the opening portion at the one of the two ends of the cylindrical portion of the cartridge body, the body-side tapered surface or the body-side curved surface becoming smaller in radial dimension toward the other of the two ends of the cylindrical portion; said piston being made of a resin and disposed inside the cylindrical portion to push out a content contained in the cylindrical portion of the cartridge body through the nozzle portion, said piston having a pair of piston-side tapered surfaces or piston-side curved surfaces formed between an annular peripheral wall surface of the piston and a pair of circular end surfaces of the piston located on both sides in a thickness direction of the piston, the pair of piston-side tapered surfaces or piston-side curved surfaces becoming smaller in radial dimension from the annular peripheral wall surface toward the pair of circular end surfaces, wherein an inner angle of the body-side tapered surface or a radius of curvature of the body-side curved surface is larger than the inner angle of the pair of piston-side tapered surfaces or the radius of curvature of the pair of piston-side curved surfaces formed on the piston; and a ratio A/B between a radial dimension A of the piston and a thickness B of the piston is $2.5 \geq A/B > 0.8$ and a ratio A/C between the radial dimension A of the piston and the inside diameter C of the cylindrical portion of the cartridge body is $1.05 \geq A/C > 1.0$;
    filling the paste dental material from the opening portion of the cartridge into the cylindrical portion by moving the opening portion of the cylindrical portion of the cartridge along a kneading surface, on which the paste dental material is kneaded, with the opening portion being inclined;
    placing the piston on the kneading surface with the circular end surface of the piston contacting the kneading surface; and
    inserting the piston into the cylindrical portion by moving the opening portion of the cylindrical portion of the cartridge closer to the piston located on the kneading surface such that the piston-side tapered surface or the piston-side curved surface of the piston is fitted into the opening portion, and thereafter moving the one of the two ends of the cylindrical portion toward the kneading surface.

* * * * *